United States Patent [19]

Harandi et al.

[11] Patent Number: 4,912,273
[45] Date of Patent: Mar. 27, 1990

[54] PRODUCTION OF AROMATIC HYDROCARBONS FROM ALKANES

[75] Inventors: Mohsen N. Harandi, Lawrenceville; Hartley Owen, Belle Mead, both of N.J.

[73] Assignee: Mobil Oil Corp., New York, N.Y.

[21] Appl. No.: 297,732

[22] Filed: Jan. 17, 1989

Related U.S. Application Data

[63] Continuation-in-part of Ser. No. 144,979, Jan. 19, 1988, abandoned.

[51] Int. Cl.[4] .................. C07C 12/02; C07C 5/333
[52] U.S. Cl. .................................... 585/322; 585/415; 585/660
[58] Field of Search .................. 585/322, 415, 660

[56] References Cited

U.S. PATENT DOCUMENTS

| | | |
|---|---|---|
| 3,296,324 | 1/1967 | Cslesery . |
| 3,374,281 | 3/1968 | Cslesery . |
| 3,756,942 | 9/1973 | Cattanach . |
| 3,760,024 | 9/1973 | Cattanach . |
| 3,835,029 | 9/1974 | Larson . |
| 3,845,150 | 10/1974 | Yan et al. . |
| 3,907,663 | 9/1975 | Owen ........................ 208/70 |
| 4,120,910 | 10/1978 | Chu . |
| 4,172,816 | 10/1979 | Pop et al. . |
| 4,350,835 | 9/1982 | Chester et al. . |
| 4,547,618 | 10/1985 | Forbus .................... 585/660 |
| 4,675,461 | 6/1987 | Owen et al. ............. 585/330 |
| 4,720,602 | 1/1988 | Chu ......................... 585/407 |

FOREIGN PATENT DOCUMENTS 0130251 1/1985 European Pat. Off. .

OTHER PUBLICATIONS

Chen et al, "M2 Forming—A Process for Aromatization of Light Hydrocarbons", *Ind. Eng. Chem. Process Des. Dev.* 25, pp. 151-155 (1986).

Primary Examiner—Curtis R. Davis
Attorney, Agent, or Firm—Alexander J. McKillop; Charles J. Speciale; Robert B. Furr, Jr.

[57] ABSTRACT

Alkanes, preferably lower alkanes, are converted to olefins in a 'third bed' external catalyst cooler (ECC) in which hot catalyst from a first regenerator ('second bed') operating in conjunction with a fluid catalytic cracker ('first bed') thermally cracks and dehydrogenates the alkanes. Because this is an endothermic reaction, the catalyst is autogeneously cooled before it is recirculated to the FCC regenerator. The cracking catalyst is the catalyst of choice in the FCC reactor. The conversion of alkanes to olefins is tailored to provide a mixed feed for an aromatization reactor ('fourth bed') which feed is proportioned to provide a substantially heat-balanced reaction in the aromatization reactor, that is, requiring no additional heat other than that which is provided by the feed and the heat of reaction. A second regenerator ('fifth bed') is provided for the aromatization reactor, preferably in a moving bed reactor system. This reactor produces a predominately aromatic hydrocarbon stream. The interrelated operation of this combination of five beds is tailored to convert all available low value alkanes and olefins to produce more valuable benzene, toluene and xylenes in the aromatic stream.

18 Claims, 1 Drawing Sheet

PRODUCTION OF AROMATIC HYDROCARBONS FROM ALKANES

CROSS-REFERENCE TO RELATED APPLICATION

This application is an continuation-in-part of U.S. patent application Ser. No. 144,979, filed Jan. 19, 1988, and now abandoned.

BACKGROUND OF THE INVENTION

This invention relates to a process in which we use an external catalyst cooler ("ECC") for dehydrogenating an alkane stream by contacting it with a fluid catalytic cracking ("FCC") catalyst to produce olefins (alkenes) and hydrogen in the ECC's effluent. This effluent containing the unreacted alkanes, hydrogen and olefins, particularly mono-olefins, is then aromatized (converted to aromatic hydrocarbons) by contacting it with a medium-pore zeolite catalyst in an aromatization ("M2-forming", or M2 for brevity) reactor, preferably operating as a moving bed. The term "medium-pore zeolite" is defined for the purpose of this disclosure to be a zeolite having a Constraint Index between about 1 and about 12.

This invention is therefore an essentially two-stage process, comprising, in the first stage, dehydrogenating and cracking a $C_{2+}$ alkane stream to a predetermined extent dictated by the demands of an M2 reactor; and, in the second stage, converting a mixture of alkanes and olefins into aromatic hydrocarbons, the ratio of the alkane/olefin components of the mixture preferably being adjusted for a substantially heat balanced reaction. By "heat balanced reaction" we do not refer to a strictly thermodynamically balanced reaction but to the operation of the M2 reactor which is not so unbalanced as to present a problem. More specifically, we refer to an aromatization reaction which preferably proceeds (a) without the addition of any heat to the reactor, and (b) at the upper limit does not cause the reactor outlet temperature to exceed about 593° C. (1100° F.), more preferably about 538° C. (1000° F.).

A key to our process is the ability to tailor operation of the ECC to provide the appropriate level of "free" heat contributed by the exothermic reactions of olefins in the M2 reactor. The olefins produced in the ECC are derived from alkanes when the ECC provides the necessary function of cooling FCC catalyst being oxidatively regenerated in a regenerator. Another key is the ability to use hot ECC effluent which contains at least 10% by volume hydrogen to operate the M2 reactor efficiently at a temperature in excess of 538° C. (1000° F.), but below a temperature which defies economic operation of the M2 reactor. By dehydrogenating the ECC alkane feed sufficiently to provide a desired olefin content, we control the temperature of the feed to the aromatization reactor to be somewhat higher than, the same as, or lower than that of the aromatization reaction.

FCC catalyst from an FCC unit is regenerated in an FCC regenerator operating at high temperature due to the high heat release of burning coke. Hot regenerated catalyst regen catalyst) is conventionally cooled in a catalyst cooler ("catcooler") by generating steam. The catcooler may be either internal or external. In this invention, we cool the regen catalyst in the ECC which functions as a dehydrogenation and cracking reactor, at the same time providing direct heat exchange because of the endothermic dehydrogenation of the alkanes fed.

Coupling the dehydrogenation of $C_{2+}$ alkanes, and particularly a lower $C_2$-$C_6$ alkane, preferably a mixture of propane ($C_3$) and butane ($C_4$) containing a minor amount by weight of olefins and $C_{5+}$ alkanes, in the ECC, with the operation of an FCC regenerator is described in greater detail for each of two modes of operation in our concurrently filed U.S. patent application Ser. No. 144,991, the disclosure of which is incorporated by reference thereto as is fully set forth herein.

FCC regenerators are designed to be "hot-operated" under pressure, that is, operated at a pressure in the range from about 25 psig to 40 psig, and as high a temperature as is practical from a materials standpoint. The temperature within a regenerator typically ranges from about 538° C. to about 815° C. (1000°–1500° F.) and the ECC operates in our process in the same general range of pressure and temperature as the regenerator. Thus, because the effluent from the ECC is available at a temperature within this range, it provides "free" heat which is of such economic benefit in the M2 reactor.

Because the dehydrogenation reaction is partly pyrolytic and partly catalytic (effect of the FCC catalyst), the FCC catalyst is referred to as "dehydrogenation catalyst" or "ECC catalyst" when it is in the ECC, and we refer to the FCC catalyst as "regen catalyst" when it is being regenerated. The thermal dehydrogenation of normally liquid hydrocarbons at a temperature in the range from 538° C. to 750° C. (1000°–1382° F.) by pyrolysis in the presence of steam is disclosed in U S. Pat. Nos. 3,835,029 and 4,172,816, inter alia; but there is no suggestion that such a reaction may be used as the basis for direct heat exchange, to cool regen catalyst in an ECC for an FCC unit, and to provide a mixture of olefins mainly mono-olefins), and paraffins mainly lower $C_2$-$C_6$ alkanes) in the ECC's effluent, fortuitously available at the "right" feed temperature for an M2 reactor, as we have now made it available in the first stage of our two-stage process. The term "olefins" is used herein, in preference to "alkenes" better to contrast with vocalized "alkanes" and minimize the confusion which may result when the latter two terms are articulated in a discussion.

The desirability of upgrading alkanes, and particularly lower alkanes, to aromatic hydrocarbons has long been recognized and exhaustively disclosed in numerous references, and particularly in U.S. Pat. Nos. 3,756,942; 3,760,024; 4,120,910 and 4,350,835. Details of the basic aromatization process are disclosed in "M2 Forming-A Process for Aromatization of Light Hydrocarbons" by N. Chen and T. Y. Yan, 25 *Ind. Eng. Chem. Process Dev.*, 151–155 (1986). The disclosures of the foregoing references are incorporated by reference thereto as if fully set forth herein. In his '942 patent Cattanach recognized that the economic handicap of a highly endothermic reaction is not easily overcome even when the feed is a $C_{5+}$ alkane and formulated a weak hydrogenation/dehydrogenation catalyst over which he could pass a mixture of alkanes and olefins, the latter to provide part of the heat for the conversion of the alkanes. The reactions in each of the '942 and '024 references are carried in the absence of added hydrogen. Conversion of lower alkanes to aromatics with a strong hydrogenation/dehydrogenation catalyst is disclosed in U.S. Pat. Nos. 3,296,324 and 3,374,281, inter alia.

The aromatization of alkanes in the presence of olefins in a substantially heat-balanced process is described in U.S. Pat. No. 3,845,150, the disclosure of which is incorporated by reference thereto as if fully set forth herein. The process uses a ZSM-5 catalyst having a silica:alumina mole ratio in the range from about 12 to 300, and the zinc ZSM-5 (the zeolite has been base exchanged with zinc ions) used therein and gallosilicoate ZSM-5 are the catalysts of choice in this invention. The aromatization to aromatic hydrocarbons is referred to as the Mobil M2-Forming Process ("M2" for brevity) and, in the prior art, is preferably conducted over HZSM-5 at moderately elevated pressure up to 1500 kPa (200 psig), and temperature in the range from about 538° C. to about 815.5° C. (1000° to 1500° F.). Though our M2 reactor may also operate in the same pressure and temperature range as in the prior art, our reactor necessarily operates at a pressure lower than 100 psia, and a temperature higher than 538° C. (1000° F.) but substantially lower than 815.5° C. (1000° to 1500° F.) for an economic advantage no other aromatization reactor we know affords.

Economical operation of an M2 reactor at this high temperature is possible because the $H_2$-containing olefinic effluent from the ECC is available at a temperature above 538° C., which in effect is a "free" preheat essential for the conversion of the alkanes, a highly endothermic reaction. Additional heat is provided in the M2 reactor by the aromatization of the olefins, which reaction is exothermic. Stated differently, the adiabatic temperature rise for alkanes is offset by that for the olefins presenting the mixture of alkanes and olefins in the olefinic effluent from the ECC.

Further, in this two-stage process the first stage will also convert light straight run ($C_5$ and $C_6$) alkanes and $C_5+$ paraffinic raffinate (such as Udex® raffinate) to olefins because the conversion of all available $C_2+$ alkanes proceeds with excellent yields at essentially the same process operating conditions of the ECC. The operation of the ECC and the olefinic effluent it produces are deliberately tailored for the specific purpose of providing the appropriately heat-balanced operation of the M2 reactor. The feed for the M2 reactor may be the ECC effluent alone, or in combination with a light straight run naphtha stream, or with a Udex® raffinate, or with a portion of an olefin-containing refinery stream (such as an FCC column $C_3$ and $C_4$ cut), any combination with the ECC effluent, and operation of the ECC being adjusted for the sole purpose of providing a heat-balanced reaction and optimum process conditions for economically producing a desired "make" of aromatic hydrocarbons.

SUMMARY OF THE INVENTION

It has been discovered that a process to convert alkanes to aromatics may be carried out economically with the operation of five reaction zones, the operation of each of which is interrelated. A "first" reaction zone is provided by the fluid bed reactor of a fluid catalytic cracker ("FCC"); a "second" reaction zone is provided by the fluid bed regenerator of the FCC unit; a "third" reaction zone is provided by a dehydrogenation reactor operating as an external catalyst cooler (ECC) to cool FCC catalyst being regenerated in the regenerator; a "fourth" reaction zone is provided by an aromatization ("M2") reactor which converts a mixture of alkanes and olefins to an aromatics-rich hydrocarbon stream; and a "fifth" reaction zone is provided by a regeneration zone for the M2 catalyst.

In particular, it has been discovered that the ECC of a regenerator for an FCC may be fed a predominantly $C_3$ and $C_4$ alkane stream, or a light straight run $C_5$ and $C_6$ stream, or a Udex® raffinate $C_5+$ stream, or a combination of all streams, and the ECC may be operated to produce a "make" of olefins in a hydrogen-containing effluent which may be combined with an alkane stream conventionally available from the FCC unit, or even another olefin-containing stream, so that the combined streams may be flowed to an M2 reactor to provide a substantially balanced heat duty. When this is done a major portion of the M2 feed is aromatized in the M2 reactor to yield an M2 product rich in BTX values.

It is therefore a general object of this invention to provide a process for utilizing excess heat extracted from hot regenerated ("regen") FCC catalyst so as simultaneously to cool the catalyst and provide a preheated feed to an M2 reactor, the process comprising transporting the hot regen catalyst from a regeneration (second) zone to a fluid bed third reaction zone; contacting the hot regen catalyst with a predominantly alkane first feedstream at a temperature in the range from about 538° C. to about 760° C. (1000° to 1400° F.) and a pressure in the range from about 239 kPa to 446 kPa (20 psig to 50 psig) to convert at least 20% of the alkanes in the first feedstream to olefins which leave the third reaction zone in a hot olefinic effluent having at least 10% by volume hydrogen; returning cooled regen catalyst to the second reaction zone; contacting the hot olefinic effluent, optionally admixed with a second feedstream containing alkanes and/or olefins in an amount preferably sufficient to produce a substantially heat-balanced reaction in the M2 reactor, with a medium-pore zeolite catalyst having an alpha in the range from 3 to about 100, at a temperature in excess of 537.8° C. (1000° F.) and a pressure in the range from 1 to 4 atmospheres, to produce a BTX-rich hydrocarbon stream.

It is a specific object of this invention to provide operation of the ECC dictated by the desired heat balance in an M2 reactor in which the feed to the M2 reactor ("M2 feed") is an olefinic effluent from the ECC containing at least 10% by volume hydrogen, preferably in a mixture with a paraffinic feedstream containing olefins, the M2 feed being preferably so proportioned that is contains a major amount of alkanes and a minor amount of olefins to provide the economical heat-balanced reaction which converts the M2 feed to an aromatics-containing stream useful as gasoline or for a chemical feedstock. The M2 reactor may be a fluid-bed or fixed-bed reactor, but is most preferably a moving-bed reactor and regenerator combination.

BRIEF DESCRIPTION OF THE DRAWING

The foregoing and other objects and advantages of our invention will appear more fully from the following description made in connection with the accompanying drawing of the preferred embodiment of the invention. The FIGURE is a process flow sheet schematically illustrating the operation of an FCC cracker, its regenerator, an ECC, a moving-bed M2 reactor and associated M2 regenerator, which together operate continuously to convert a lower alkane-containing feed to the ECC into an olefin-containing effluent which is optionally modulated with additional alkanes and/or olefins to provide a heat-balanced aromatization reaction in the M2 reactor.

DETAILED DESCRIPTION OF THE PREFERRED EMBODIMENT

In its preferred embodiment, the process is a two-stage process, the first comprising converting a first alkane feedstream to an olefin-containing effluent, and the second stage comprising combining the olefin-containing effluent with a second alkane and/or olefin feedstream to provide an M2 feed which preferably provides a substantially "heat-balanced reaction" in the M2 reactor.

In the ECC, heat for the endothermic, and at least partially pyrolytic, reaction for converting the $C_2$–$C_6$ lower alkanes in the first alkane stream to lower olefins, mainly ethene, propene and butenes, is supplied by hot spent FCC catalyst which is being regenerated. By adding a predetermined quantity of the olefin-containing effluent to the second alkane stream to be aromatized in the M2 reactor, the highly endothermic reaction of alkanes being aromatized is modulated by the exothermic reaction of olefins being aromatized. Thus, the reactor may operate with a substantially neutral or "balanced" heat duty.

We therefore provide a two-stage process for utilizing heat extracted from a hot regeneration ("regen") catalyst so as simultaneously to cool the regen catalyst and preheat a feedstream ("M2 feed") to an M2 reactor, in five reaction zones cooperating continuously to produce an aromatic hydrocarbon-containing stream. In a first reaction zone, gas oil range hydrocarbons, or "resid", is cracked utilizing a first fluid bed of large pore rare earth impregnated Y-faujasite FCC catalyst; in a second reaction zone, spent FCC catalyst is oxidatively regenerated; in a third reaction zone, an external catalytic cooler autogeneously cools regenerated FCC catalyst by dehydrogenating the first lower alkane stream to produce an olefinic effluent; in a forth reaction zone, the olefinic effluent is preferably combined with a paraffinic and/or olefinic stream and the combined streams are aromatized over a medium-pore zeolite catalyst having an alpha (activity) in the range from about 3 to about 100; and, in a fifth reaction zone, the medium-pore aromatization catalyst is oxidatively regenerated.

The term "reaction zone" is intended to indicate the totality of the equipment employed in the conversion step, wherein the feed hydrocarbons are passed through a reaction chamber(s) which may contain several beds of catalyst, interstage heaters, etc.

The two-stage process comprises a first stage, including (a) utilizing excess heat from said second reaction zone by transporting hot regenerated FCC catalyst from the second reaction zone to a third reaction zone located externally relative to the second reaction zone; (b) contacting the hot FCC catalyst with the first lower alkane stream in the third reaction zone at superatmospheric pressure and a temperature below that of the second reaction zone, for a time sufficient to provide conversion of the alkanes to olefins which leave the third reaction zone in the olefinic effluent containing at least 10% by weight hydrogen; (c) returning a predetermined amount of FCC catalyst from the third reaction zone to the first or second reaction zones at a temperature below the operating temperature of the second reaction zone; and a second stage, including (d) flowing the olefinic effluent from the third reaction zone, optionally in combination with a predetermined amount of alkanes and/or olefins sufficient to provide a heat-balanced reaction to a fourth reaction zone for aromatizing alkanes and olefins to aromatic hydrocarbons; (e) contacting the olefinic effluent with a medium-pore zeolite catalyst effective to aromatize the alkanes and olefins at a WHSV in the range from 0.1 to 50 $hr^{-1}$, with a reactor outlet temperature in excess of 538° C., preferably in the range from about 540° C. to about 593° C. (1000°–1100° F.) under superatmospheric pressure up to about 4 atm, to an aromatics-rich hydrocarbon stream; and, (f) recovering a hydrocarbon stream rich in BTX values from the effluent of the fourth reaction zone.

By "aromatic hydrocarbons" and "BTX values" we refer not only to benzene, toluene and xylene, but also to ethyl benzene, cumene, methylethyl benzene, trimethyl benzenes, methylpropyl benzenes, indane, $C_{11}$ alkylbenzenes, naphthalene, methyl naphthaalene, and the like which are formed in small amounts relative to the BTX.

The First Stage: Operation of the ECC

In the preferred embodiment of the invention, a first $C_2$–$C_6$ lower alkane stream which may contain a minor amount of olefins is fed to the ECC, and the ECC is operated to provide the "correct" olefinic content in the effluent which is to be added to the M2 feed. If desired, the ECC effluent may be supplemented with either additional alkanes or olefins, whichever is necessary to provide a feed for a heat-balanced reaction.

In the first stage, the ECC utilizes excess heat from the regeneration zone of an FCC unit for the dehydrogenation reaction. Hot regenerated FCC catalyst from the regeneration zone is transported to the ECC, and the hot FCC catalyst is contacted in the ECC with a $C_2$–$C_6$ lower alkane at an elevated temperature sufficient to provide the catalytic conversion of a major portion by weight of the alkanes to olefins.

The preferred operation of the ECC typically produces hydrogen and $C_3$–$C_6$ mono-olefins, including at least 20% light $C_2$–$C_4$ olefins, the total $C_2$–$C_6$ olefins typically being in the range from about 30 to 60% by weight. Non-deleterious components, such as methane and other unreacted alkanes and inert gases, will be present in the effluent. The preferred feed to the ECC contains more than 80 wt. % $C_3$–$C_5$ lower aliphatic hydrocarbons.

It is this entire content of the ECC effluent which is to be upgraded to high octane gasoline containing aromatics, preferably at least 50% by weight aromatics. The desired products are $C_6$ to $C_{12}$ aromatics which will comprise at least 50 wt. %, and preferably 65% or more, of the product recovered from the M2 reactor, and may include $C_4^+$, preferably $C_4$–$C_{10}$, and more preferably $C_6$–$C_{10}$ cycloaliphatic, paraffinic and olefinic hydrocarbons.

The Second Stage: Operation of the "M2" Aromatization Reactor

In the second stage, the olefin-containing effluent from the ECC is optionally combined with a second lower alkane and/or olefinic feedstream and flowed to a M2 reactor for aromatizing the alkanes and olefins to produce an aromatics-rich stream. In the M2 reactor the combined stream of olefins and lower alkanes is contacted with a suitably modified medium-pore zeolite catalyst, of which ZSM-5 is an example, effective to aromatize the olefins and alkanes to aromatics, cycloaliphatics and other gasoline range hydrocarbons having a boiling point in the range from about 75° C. to about 260° C. (200°–500° F.). The aromatization of the olefins provides just enough heat to supply the additional heat duty for the aromatization of the alkanes. Spent catalyst from the M2 reactor is regenerated in the M2 regenerator and returned to the M2 reactor.

The reaction severity conditions in the M2 reactor can be controlled to optimize yield of $C_{6}+$ aromatic hydrocarbons. It is understood that aromatics production is promoted by those zeolite catalysts having a high concentration of Bronsted acid reaction sites. Accordingly, an important criterion is selecting and maintaining catalyst inventory to provide either fresh catalyst having acid activity or by controlling catalyst deactivation and regeneration rates to provide an apparent average alpha value of about 5–80, more preferably from 10–20.

Techniques for incorporating zeolites into a matrix are conventional in the art and are set forth in U.S. Pat. No. 3,140,253.

Catalysts

The members of the class of zeolites useful herein have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolite ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732 discloses Constraint Index values for typical zeolite materials and is incorporated by reference as if set forth at length herein.

In a preferred embodiment, the catalyst is a zeolite having a Constraint Index of between about 1 and about 12. Examples of such zeolite catalysts include ZSM-5, ZSM-11, ZSM-12, ZSM-22, ZSM-23, ZSM-35 and ZSM-48.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous ZSM-5); 4,100,262 and 4,139,600, the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof ar described in U.S. Pat. No. 3,832,449, the disclosure of which is incorporated herein by reference. Zeolite ZSM-23 and the conventional preparation thereof are described in U.S. Pat. No. 4,076,812, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 1,107,195, the disclosure of which is incorporated herein by reference. Zeolite ZSM-48 and the preparation thereof are taught in U.S. Pat. No. 4,375,573, the disclosure of which is incorporated herein by reference.

It is known that zeolites, particularly synthetic zeolites, can have their composition modified by impregnating certain metals thereonto and/or thereinto. The composition can also be modified by exchanging various anions and/or cations into the crystal structure of the zeolite, replacing more or less of the ions originally present upon production of the zeolite.

Medium pore zeolites, more specifically, those zeolites having a Constraint Index of between about 1 and about 12, have been found to be especially active for aromatization, if they have at least a portion of the original cations associated therewith replaced by any of a wide variety of other cations according to techniques well known in the art. Typical replacing cations would include hydrogen, ammonium, and metal cations, including mixtures of the same. Of the replacing cations, preference is given to cations of hydrogen, ammonium, rare earth, gallium, magnesium, zinc, calcium, nickel, platinum and mixtures thereof. Particularly effective medium-pore zeolites are those which have been base exchanged with hydrogen ions, ammonium ions, zinc ions or mixtures thereof. Most especially zinc-containing zeolite having the structure of ZSM-5 is the best presently known catalyst for aromatizations as set forth.

Typical ion exchange techniques would be to contact a medium-pore zeolite with a salt of the desired replacing cation or cations. Although a wide variety of salts can be employed, particular preference is given to chlorides, nitrates and sulfates.

Representative ion exchange techniques are disclosed in a wide variety of patents, including U.S. Pat. Nos. 3,140,249; 3,140,251; 3,140,253 and 3,845,150, the disclosures of which are incorporated by reference thereto as if fully set forth herein.

It is also within the scope of the aromatization process to which this application is directed to incorporate a desired metallic component onto the medium-pore zeolites by techniques other than ion exchange. Thus, for example, it is possible to impregnate a desired metallic component, such as zinc, platinum or palladium, thereinto by conventional impregnation techniques, as well as merely depositing the elemental metal onto the particular zeolite and, in some cases, such as with zinc oxide, to incorporate the metal by physical admixture of the zeolite with an insoluble metal compound.

In any event, following contact with a salt solution of the desired replacing cation, the zeolites are preferably washed with water and dried at a temperature ranging from 68° C. to about 316° C. and thereafter heated in air or inert gas at temperatures ranging from about 260° C. to 816° C. for periods of time ranging from 1 to 48 hours or more. It is noted that this heat treatment can be carried out in situ, i.e. while the particular aromatization reaction is taking place, but it is preferred to carry it out as a separate step prior to carrying out the aromatization reaction.

The most preferred crystalline zeolite has a composition, in terms of mole ratios of oxides, as follows:

$$0.9 + 0.2 M_{2/n}O : Al_2O_3 : Y\ SiO_2 : z\ H_2O$$

wherein M is at least one cation having a valence n, Y is at least 5 and z is between 0 and 40 and having the X-ray diffraction lines as set forth in Table 1 of U.S. Pat. No. 3,760,024.

It has also recently been discovered that medium-pore zeolites have unusual activity for catalyzing the cyclization of aliphatic compounds into aromatic rings and, under appropriate reaction conditions, alkylating these or other rings while being substantially inert with respect to aromatic rings themselves. U.S. Pat. No. 3,756,942, and U.S. patent application Ser. No. 253,942, filed on May 17, 1972 amply describe and claim these unusual aromatization capabilities for zeolites having the structure of ZSM-5.

According to these prior references, the substance of which are incorporated herein by reference, suitable $C_2+$ hydrocarbon feed materials boiling up to about 204° C. (400° F.) are contacted with a medium-pore zeolite catalyst at about 538° C. (1000° F.) to 816° C. (1500° F.) depending upon the feed composition, at weight hourly space velocities (WHSV) ranging from 0.1 to 50 $hr^{-1}$, preferably from 0.5 to 5 $hr^{-1}$, under such combination of conditions as to convert the feed to a mixed product comprising vapor and, under preferred conditions, a major amount by weight of aromatic liquid. Though the moving-bed reactor system may produce as little as about 30 gms of liquid predominantly aromatic product per 100 gms of feed, it is preferred to run it under process conditions which produce 65 gms of aromatics per 100 gms of feed.

As in many prior art applications, the supplemental feed material to be aromatized with the ECC effluent may comprise paraffins, olefins and/or naphthenes, and may be derived from various refinery streams, e.g. coker gasoline, naphthas, reformate, pyrolysis gasoline, etc. As a general proposition, aromatization of any relatively low value stream may be "piggy-backed" with the ECC effluent so that our two-stage process is principally viewed not only as one for upgrading the octane value of various refinery streams boiling in the gasoline range by converting some of the low octane components thereof into high octane aromatic, but also as one which benefits the basic operation and economics of the FCC unit.

In accord with, and fulfilling the object of providing an economic operation of five reaction zones cooperating to produce aromatic hydrocarbons from a mixture of alkanes (saturates) and olefins (unsaturates) so proportioned that the M2 feed contains about 30 to 65% alkanes, and about 20% to less than 60% by weight olefins, the best embodiment of this invention comprises aromatizing the mixture by contacting it with a coarse aluminosilicate zeolite having the structure of ZSM-5 in a moving-bed reaction zone under appropriate temperature, pressure and space velocity conditions to cause conversion of a major proportion by weight preferably more than 65% by weight, of the hydrocarbon M2 feed, to new aromatic compounds. It has been found that, if the first predominantly alkane feedstream is carefully processed in the ECC, the endothermicity formerly attributed to this aromatization reaction is overcome and the reaction can be accomplished in a heat balanced manner.

According to this invention, the aromatization reaction may be carried out with an upflow fixed bed reactor with catalyst particles containing ZSM-5 of 1.587 mm (0.0625") to 3.17 mm (0.125") diameter; or a fluidized bed in which ZSM-5-containing catalyst particles, about 50 to 400 mesh, are used, but, as stated hereinabove in the best mode the reaction is carried out in the vapor phase in a reaction zone containing a moving catalyst bed.

The configuration of the moving-bed M2 reaction zone and associated M2 regenerator is not a basic element of this invention; this configuration happens to be surprisingly effective for the second stage of our process because moving beds such as have been used in the Thermofor® Catalytic Cracking (TCC) units, and such as are widely used currently for the reforming of naphtha fractions, are particularly well-adapted to the process conditions deemed optimum for our process.

The preferred moving-bed reactor system employs a spherical catalyst having a diameter in the range from 1.587 mm (0.0625") to 6.34 mm (0.25"), and the catalyst contains from about 0.01 to 3. wt. %, preferably 0.3 to 1.0 wt. % gallium. A multi-stage moving-bed operating system may be used having two or more reactors in sequence with provision for interstage heating, if necessary, to replace the heat of reaction when the overall reaction proceeds endothermically.

The reactor inlet temperature is preferably about 619° C. to 701° C. (1200° to 1300° F.), and the reactor outlet temperature is preferably in the range from about 538° C. to 593° C. (1000° to 1100° F.), and the reactor pressure from about 170 kPa to 446 kPa (10 to 50 psig). The reaction mixture suitably passes through the reaction zone at a WHSV of about 0.1 to 50 $hr^{-1}$, more preferably from 0.5 to 5 $hr^{-1}$.

Within the foregoing general parameters, one skilled in the art of petroleum and petrochemical design may determine proper operating conditions, vessel designs, and operating procedures for the process by the use of standard process design techniques.

The preferred feed to the heat balanced process of this invention is suitably a mixture of the ECC effluent, and/or a predominantly saturated stream, and/or a predominantly olefinically unsaturated stream. Suitable examples of unsaturated feed streams to the M2 reactor are light ends from cracking or coking units (for example the stream that might otherwise be used as feed to a refinery alkylation unit); coker gasoline; cracked gasoline and pyrolysis gasoline (for example, the liquid product evolved from naphtha cracking to produce olefins). Other examples of this portion of the feed are olefins themselves in pure or impure form, e.g. ethylene, propylene, butylenes, hexylenes, cracked gasoline, etc. The saturated portion of this feed mixture can be supplied by such refinery streams as light reformate, full range reformate, Udex® raffinate, Fischer-Tropsch gasoline, full range naphtha, etc.

Taking the mixed M2 feedstream as a whole, it should have an analysis of at least 10% by volume hydrogen, and about

| | |
|---|---|
| Alkanes (saturates) | 30–85 |
| Olefins (unsaturates) | 15–70 |

It may also contain a small proportion of aromatics. The aromatics are substantially inert with respect to the ZSM-5 under the aforementioned aromatization conditions. If present, it is probable that a small amount of the aromatics will be alkylated during the second stage of the process.

The aromatization process of this invention is more efficient and economical than any previously described because the heat input is substantially zero; yet in the best mode, it converts economically disadvantageous, low octane saturates to economically attractive high octane aromatics in a yield of at least about 50 gms of new aromatics per 100 gms of saturated feed, while also upgrading olefinic feeds to aromatics in the context of commercial reality.

It is known that during aromatization reactions of the type described in the prior art, the medium-pore zeolite catalyst becomes coated with coke which tends to progressively diminish the activity of the catalyst to such an extent that it is necessary to regenerate it. This regeneration can be accomplished in the same vessel in which the aromatization is carried out by stopping the feed of hydrocarbon reactant, or in a separate reactor into the regenerator as in fluid catalytic cracking. Though this can be accomplished in the usual manner by burning off the coke with air or by gasifying it with hydrogen, it is much preferred to keep the coke "make" to as low a level as possible. It is now possible to do this in our process because a portion of the alkanes previously responsible for the coke make are converted to olefins in the ECC. The coke make is therefore substantially lessened. Also contributing to a lower coke make is the relatively lower temperature at which we can now effect a high degree of conversion.

Moreover, since a large portion, if not all, of the M2 feed passes through the ECC, contaminants normally associated with the ECC feedstream (first predominantly alkane feedstream) are adsorbed on the ECC catalyst which has a high propensity for such adsorption of contaminants. Because the catalyst with adsorbed contaminants is then regenerated in the FCC regenerator, the contaminants are disposed of without posing the otherwise serious threat to the active life of the M2 catalyst.

Figure 1:
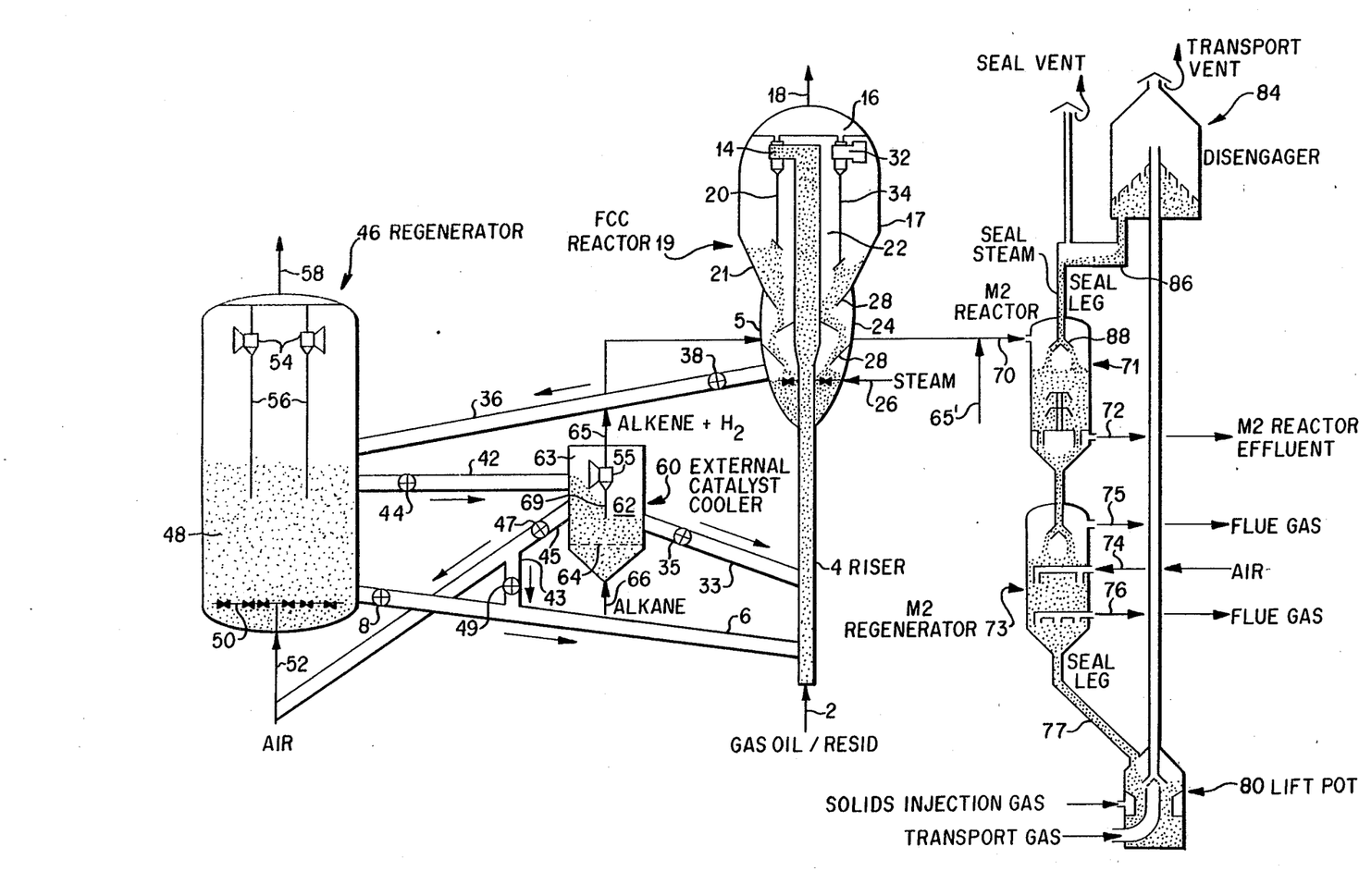

Referring now to the drawing, there is schematically illustrated a flowsheet in which a charge stock (feed) 2, such as gas oil (boiling range 315.5°–676.7° C. or 600°–1200° F.), is introduced, after it is preheated, into riser 4, near the bottom. The gas oil is mixed with hot regen catalyst, such as zeolite Y, introduced through a valved conduit means such as standpipe 6 provided with a flow control valve B. Because the temperature of the hot regenerated catalyst is in the range from about 676.7° C. (1200° F.) to about 732.2° C. (1350° F.), a suspension of hydrocarbon vapors is quickly formed, and flows upward through the riser 4.

The riser 4 is flared gently outward into a region 5 through which catalyst and entraned hydrocarbons are flowed, being afforded, in this region 5, the contact time preselected to provide desired cracked products. Catalyst particles and the gasiform products of conversion continue past region 5 and are discharged from the top of the riser into one or more cyclone separators 14 housed in the upper portion 17 of the vessel, indicated generally by reference numeral 19. Riser 4 terminates in a 'bird cage' discharge device, or an open end "T" connection may be fastened to the riser discharge which is not typically directly connected to the cyclonic catalyst separation means. The effluent from riser 4 comprises catalyst particles and hydrocarbon vapors which are led into the cyclonic separators 14 which effect separation of catalyst from hydrocarbon vapors. Such vapors pass into a plenum chamber 16 and thence are removed through conduit 18 for recovery and further processing.

Hydrocarbon vapors from cyclone 14 are discharged to a plenum chamber 16 from which they flow through conduit 18 for further processing and recovery, typically to a fractionator column where the products of racking are separated into preselected fractions.

Catalyst separated from the vapors descends through dipleg 20 to a fluid bed 22 of catalyst maintained in the lower portion 21 of the vessel 19. The bed 22 lies above, and in open communication with a stripping zone 24 into which the catalyst progresses, generally downward, and countercurrent to upflowing inner gas, usually steam, introduced through conduit 26. Baffles 28 are provided in the stripping zone to improve stripping efficiency.

Spent catalyst, separated from the hydrocarbon vapors in the cyclones, is maintained in the stripping zone 24 for a period of time sufficient to effect a higher temperature desorption of feed-deposited compounds which are then carried overhead by the steam. The stripping zone is maintained at a temperature of about 1250° F. or even higher, if hot regenerated catalyst is introduced into the stripping zone by means not shown as is sometimes done. The steam and desorbed hydrocarbons pass through one or more cyclones 32 which return catalyst fines through dipleg 34 to the bed 22.

Stripped catalyst flows though conduit 36, provided with flow control valve 38, to regenerator 46 containing a dense fluid bed 48 of catalyst into the lower portion of which bed, regeneration gas, typically air, is introduced by distributor 50 supplied by conduit 52. Cyclone separators 54 provided with diplegs 56 separate entrained catalyst particles from flue gas and return the separated catalyst to the fluid bed 48. Flue gases pass from the cyclones into a plenum chamber and are removed therefrom by conduit 58. Hot regenerated catalyst is returned to the bottom of riser 4 by conduit 6 to continue the process with another conversion cycle, all of which is conventionally practiced.

The hot regen catalyst flows though conduit 42, provided with flow control valve 44, to ECC 60 containing a fluid bed 62 of ECC catalyst. As schematically illustrated, the ECC is coupled to the regenerator through the catalyst transfer lines but is physically located externally relative to both the regenerator and the cracker. Into the lower portion of the ECC bed is introduced the ECC feedstream of lower alkanes to be dehydrogenated. Most preferred is a stream in which propane is the major constituent relative to the amount of butanes and also to the total weight of other hydrocarbon components. The alkane feed is supplied by distributor 64 fed through conduit 66, typically comprising propane and minor amounts of butanes and other lower alkanes, and even smaller amounts of olefins scavenged from various waste refinery streams. The hot stream of regen catalyst withdrawn from the regenerator is quickly cooled by direct contact with the relatively cool gases and catalyst in the ECC bed.

The ECC generally operates at relatively low WHSV in the range from 0.01 to 10 $hr^{-1}$, preferably from 0.1 to 1.0 $hr^{-1}$, and in a relatively narrow pressure and temperature range from above 20 psig to about 50 psig (239–116 kPa), preferably 25 psig to about 45 psig (273–411 kPa), and from about 649°–815.5° C. (1200° to 1500° F.), preferably 732° C. (1350° F.), respectively, depending upon the pressure and temperature at which the FCC regenerator is operated.

The amount of heat supplied to the ECC is determined by a controlled amount of catalyst withdrawn from the regenerator. The rate at which the catalyst stream is withdrawn depends upon the temperature at which the regenerator is to be operated, which in turn determines the amount of alkanes which may be dehydrogenated. For a given flow of regenerated catalyst to the ECC at a preselected temperature, and a given rate of lower alkane charged, the temperature of catalyst in the ECC is controlled in the range from about 593°–732° C. (1100° to 130° F.) by the temperature to which the charge is preheated Cyclone separators 55 provided with a dipleg 69 separates entrained catalyst particles from ethylene, propylene, hydrogen, butylenes, other hydrocarbon products, and unconverted alkanes, and return the separated catalyst to the fluid bed 62. However, it is preferred to use sintered metal filters as well, to prevent fines from leaving the ECC with the effluent and contaminating the M2 catalyst. The products of conversion of the dehydrogenation reaction pass from the cyclones into a plenum chamber 63 and are remove therefrom by effluent line 65. Relatively cool ECC catalyst is returned to the regenerator 46 through conduit 45 provided with a valve 47, by being lifted with air in the air-lift conduit 52. If desired, the regenerator may be partly or completely bypassed by flowing the cooled catalyst from the ECC through conduit 33, provided with valve 35, to the riser 4. For greater flexibility of operation, a portion of the cooled catalyst from the ECC is returned to the regenerator through line 45, and the remainder flowed through line 33 to the riser.

Regenerated catalyst is removed from the regenerator through return conduit 6 controlled by valve 8, for passage to the riser 4 of the cracker either above or below the point where line 33 communicates with the riser. This bypassing of the regenerator by directly flowing cooled catalyst to the FCC riser is desirable in cases where maximizing catalyst circulation and minimizing thermal cracking because of the relatively low catalyst temperature in the FCC riser, is desired.

Again, for additional flexibility of operation, cooled catalyst from the line 45 may be flowed through conduit 43, controlled by valve 49, into the return conduit 6.

The effluent 65 from the ECC (third reaction zone) is supplemented with supplemental alkane/olefin feed (for heat-balanced reaction) in line 65', and the mixture flowed through feed line 70 to the M2 reactor (only one is shown) where it is contacted with down-flowing catalyst and, upon being converted to aromatics, leaves through reactor effluent line 72. The catalyst flows from the reactor 71 to kiln regenerator 73 where it is contacted with air introduced through line 74. Flue gas from the kiln regenerator leaves through lines 75 and 76 and is disposed of.

Regenerated M2 catalyst flows out of the kiln 73 through a seal leg 77 into a lift pot 80. The seal leg comprises a vertical pipe to contain the downward-flowing packed bed of catalyst particles, of sufficient length to offer relatively high resistance to, and thereby minimize, any counterflow of gas. In the lift pot 80 a small air stream is used to push the particles into the path of a high-velocity stream of transport air which carries them up through standpipe 82, into a disengager drum 84. The transport air is vented and the particles shower down onto an inclined perforated plate designed to minimize segregation of coarse catalyst and any fines produced by attrition.

The catalyst flows by gravity through another seal leg 86 and is returned to the reactor 71. Though not shown, a side stream is continually withdrawn from this seal leg 86 and is elutriated to remove fines which could otherwise accumulate and reduce gas throughput capacity. The catalyst enters the reactor 71 through a multiplicity of tubes 88 with bell-shaped ends, again to minimize segregation, and leaves the reactor through a multiplicity of similar tubes, flowing to the regenerator to complete the cycle.

Product and flue gases from the reactor and kiln are withdrawn either from above the catalyst bed levels, or from any point within the bed by means of a simple inverted-trough arrangement (not shown). As long as the superficial gas velocity passing through the catalyst surface at the entrance of an inverted drawoff trough is insufficient to fluidize the particles, they will not rise up into the trough and try to leave with the exit gases.

EXAMPLE

In a specific embodiment of the invention, 3800 BPSD (barrels/stream day) of $C_3$–$C_4$ alkanes are fed to the ECC operating at 699° C. (1290° F.). Approximately 40% of this stream is converted to $C_2+$ olefins and the olefinic effluent contains more than 15% by volume hydrogen. 2700 BPSD of predominantly paraffinic FCC PP streams (30% olefinic) are combined with the olefinic effluent from the ECC and fed to the M2 reactor. The M2 reactor operates with an additional heat input and provides approximately 2200 BPSD of $C_5+$ gasoline range hydrocarbons with more than 50% aromatics. The $C_6+$ portion, used as gasoline, has a research octane number (RON) of 110.

In an analogous manner, with a little trial and error such as is expected of one skilled in the art, the operation of the ECC and of the M2 reactor is adjusted to convert a large number of combinations of alkane- and olefin-containing streams which are proportioned to aromatize the M2 feed with no heat introduced from an additional heat source and yield the desired aromatic content in the M2 product stream most economically.

Having thus provided a general discussion, described the dehydrogenation/cracking of an alkane feedstream in the ECC to produce an olefinic effluent which may optionally be mixed with an alkane and/or olefin stream and aromatized to a BTX stream in the gasoline range, and set forth a specific illustration of the present invention in an example in support thereof, it is to be understood that no undue restrictions are to be imposed by reason thereof except as provided by the following claims.

What is claimed is:

1. In a process for upgrading hydrocarbons in at least five reaction zones continuously cooperating to produce aromatic hydrocarbons from a first feedstream of $C_2+$ alkanes, including a first reaction zone utilizing a large-pore FCC crackIng catalyst to crack gas oil range hydrocarbons, a second reaction zone in which said large-pore catalyst is oxidatively regenerated, a third reaction zone in which an external catalyst cooler autogeneously cools regenerated catalyst by dehydrogenation of said first alkane feedstream to produce an olefinic effluent, a fourth reaction zone containing a catalyst comprising a zeolite having a Constraint Index of between about 1 and about 12, in which fourth zone said olefinic effluent optionally admixed with a second feedstream of alkanes and/or olefins is aromatized to said aromatic hydrocarbons, and a fifth reaction zone wherein said aromatization catalyst is oxidatively regenerated, a two-stage process comprising a first stage including:
(a) utilizing excess heat from said second reaction zone by transporting hot regenerated FCC catalyst from the second reaction zone to a third reaction zone located externally relative to the second reaction zone;
(b) contacting said hot FCC catalyst with said first feedstream in said third reaction zone at superatmospheric pressure, and a temperature below that of said second reaction zone, for a time sufficient to provide conversion of at least 20% by weight of alkanes in said first feedstream to olefins, which leave said third reaction zone in said olefinic effluent;
(c) returning a predetermined amount of FCC catalyst from said third reaction zone to said first or second reaction zones at a temperature below the operating temperature of said second reaction zone; and a second stage including:
(d) flowing the olefinic effluent, containing at least 10% by volume of hydrogen, from the third reaction zone to said fourth reaction zone, optionally in admixture with a predetermined amount of alkanes and/or olefins in said second feedstream, to form a mixture of alkane and olefin fractions so proportioned that mixed feed to said fourth reaction zone contains about 40% to 65% alkanes and a substantial amount by weight of olefins sufficient to operate said fourth reaction zone without heat from a source other than said mixed feed;
(e) contacting said mixed feed with said catalyst comprising a zeolite having a Constraint Index of between about 1 and about 12 effective to aromatize the alkanes and olefins in said mixed feed at a temperature in the range from about 538° C. to about 760° C. (1000°–1400° F.) under superatmospheric pressure, and at a WHSV in the range from 0.05 to 50 hr$^{-1}$, in the fourth reaction zone, to convert said mixed feed into an aromatics-rich hydrocarbon steam;
(f) recovering the aromatics-rich hydrocarbon stream rich in BTX values from the effluent of said fourth reaction zone; and
(g) returning a predetermined amount of said catalyst comprising a zeolite having a Constraint Index of between about 1 and about 12 from said fifth reaction zone to said fourth reaction zone.

2. The process of claim 1 wherein said zeolite has the structure of at least one selected from the group consisting of ZSM-5, ZSM-11, ZSM-12, ZSM-22, ZSM-23, ZSM 35 and ZSM-48.

3. The process of claim 2 wherein said zeolite has the structure of ZSM-5.

4. The process of claim 2 wherein said zeolite contains zinc.

5. The process of claim 1 wherein said first alkane feedstream contains predominantly $C_2$–$C_6$ lower alkanes selected from a stream consisting essentially of propane and butanes ($C_3$ and $C_4$) in LPG; pentanes, hexanes ($C_5$ and $C_6$) in light straight run; pentanes, hexanes, heptanes and heavier ($C_5$, $C_6$, $C_7+$) and a mixture of two or more of the foregoing streams.

6. The process of claim 5 wherein said third reaction zone is provided by the external catalyst cooler operating at a pressure in the range from about 239 to 411 kPa (20 to 50 psig) and a temperature in the range from about 538° C. to about 760° C. (1000°–1400° F.).

7. The process of claim 6 wherein spent catalyst from said fourth reaction zone is oxidatively regenerated in said fifth reaction zone at a temperature in the range from about 371° C. (700° F.) to about 704° C. (1300° F.) for a time sufficient to oxidize carbonaceous deposits on the catalyst and regenerated medium pore catalyst is returned having a carbon content in the range from 0 to 5% by weight, from said fifth reaction zone to said fourth reaction zone.

8. The process of claim 7 wherein said fourth and fifth reaction zones are provided by a moving-bed reactor.

9. A two-stage process for converting $C_2+$ alkanes to olefins which are in turn converted to an aromatic hydrocarbon-containing stream comprising:
(a) passing a first predominantly lower alkane feedstream into a dehydrogenation zone containing a large-pore zeolite catalytic cracking catalyst at superatmospheric pressure less than about 689 kPa (100 psia) and a temperature in the range from about 538° C. to about 760° C. (1000°–1400° F.) for a period of time sufficient to convert at least 20% by weight of the alkanes in said first feedstream to olefins which leave said dehydrogenation zone in an olefinic effluent containing alkanes and olefins so proportioned as to contain about 40% to 65% alkanes and a substantial amount by weight of olefins sufficient to operate an aromatization zone without heat from a source other than said alkanes and olefins;
(b) contacting said olefinic effluent containing at least 10% by volume hydrogen in said aromatization zone containing a crystalline medium-pore zeolite catalyst effective to aromatize a major portion by weight of the alkanes and olefins to aromatic hydrocarbons, at superatmospheric pressure, at a WHSV in the range from 0.05 to 50 hr$^{-1}$, and a temperature in excess of 537.8° C. but below a temperature deleterious to the catalyst; and
(c) recovering an aromatics-rich hydrocarbon stream from the effluent of said aromatization zone.

10. The process of claim 9 wherein said first lower alkane feedstream includes a major amount by weight of propane in relation to the total weight of other hydrocarbons.

11. The process of claim 10 wherein said large-pore zeolite cracking catalyst includes a catalytic amount of a metal or metal oxide of an element from Group V or VIII sufficient to enhance the dehydrogenation activity of said large-pore catalyst.

12. The process of claim 10 wherein said medium-pore zeolite has a Constraint Index of between about 1 and 12.

13. The process of claim 12 wherein said medium-pore zeolite has the structure of at least one selected from the group consisting of ZSM-5, ZSM-11, ZSM-12, ZSM-22, ZSM-23, ZSM-35 and ZSM-48.

14. The process of claim 10 wherein said medium-pore zeolite is characterized by a composition, in terms of mole ratios of oxides, as follows:

$0.9 \pm 0.2 M_{2/n}O : Al_2O_3 : Y\ SiO_2 : z\ H_2O$ wherein M is at least one cation having a valence n, Y is at least 5 and z is between 0 and 40, and having the X-ray diffraction lines as set forth in Table 1 of U.S. Pat. No. 3,760,024.

15. The process of claim 14 wherein said aromatization zone is provided by a moving-bed M2 reactor and associated M2 regenerator.

16. The process of claim 15 wherein said dehydrogenation zone is operated to provide said olefinic effluent with a proportion of alkanes/olefins such that it is augmented with a second feedstream containing alkanes and/or olefins in an amount sufficient to provide a mixed feed to said aromatization zone in which the reaction is substantially heat balanced.

17. The process of claim 16 wherein said dehydrogenation zone is operated to provide a maximum olefinic content in said olefinic effluent and said olefinic effluent to said second stage is augmented with a predominantly $C_5$–$C_6$ raffinate.

18. The process of claim 14 wherein said WHSV of the mixture fed to the moving-bed reactor is in the range from 0.5 to 5.0 $hr^{-1}$ and said aromatics-rich hydrocarbon stream contains a major amount by weight of aromatics.

* * * * *

UNITED STATES PATENT AND TRADEMARK OFFICE
CERTIFICATE OF CORRECTION

PATENT NO. : 4,912,273
DATED : 3/27/90
INVENTOR(S) : M.N. Harandi et al

It is certified that error appears in the above-identified patent and that said Letters Patent is hereby corrected as shown below:

| | |
|---|---|
| Col. 1, line 64 | insert --(-- before "regen" |
| Col. 2, line 36 | insert --(-- before "mainly" |
| Col. 2, line 36 | insert --(-- before "mainly" |
| Col. 5, line 37 | "forth" should be --fourth-- |
| Col. 8, line 5 | "4,076,812" should be --4,076,842-- |
| Col. 8, line 10 | "1,107,195" should be --4,107,195-- |
| Col. 8, line 1 | "ar" should be --are-- |
| Col. 9, line 5 | "$0.9 + 0.2M_2$" should be --$0.9 \pm 0.2M_2$-- |
| Col. 10, line 30 | "619°" should be --649°-- |
| Col. 10, line 31 | "701°C" should be --704°C-- |
| Col. 11, line 52 | "B" should be --8-- |
| Col. 13, line 1 | "(239-116kPa)" should be --(239-446 kPa)-- |
| Col. 13, line 16 | "130°F" should be --1350°F-- |
| Col. 13, line 27 | "remove" should be --removed-- |

Signed and Sealed this

Twentieth Day of August, 1991

Attest:

HARRY F. MANBECK, JR.

*Attesting Officer*   *Commissioner of Patents and Trademarks*